United States Patent [19]
Lezdey et al.

[11] Patent Number: 5,532,215
[45] Date of Patent: Jul. 2, 1996

[54] ANTIVIRAL COMPOSITIONS AND METHOD OF USE

[76] Inventors: John Lezdey, 976 Kingston Dr., Cherry Hill, N.J. 08034; Allan Wachter, 9822 S. Grandview, Tempe, Ariz. 85284

[21] Appl. No.: 322,293

[22] Filed: Oct. 3, 1994

Related U.S. Application Data

[63] Continuation-in-part of Ser. No. 953,234, Sep. 30, 1992, abandoned, and a continuation of Ser. No. 122,204, Sep. 15, 1993, Pat. No. 5,376,633.

[51] Int. Cl.$^6$ .......................... A61K 38/16; A61K 38/48
[52] U.S. Cl. .................. 514/8; 514/12; 514/886; 514/887; 530/395; 424/78.07; 424/94.64; 435/69.2; 435/236
[58] Field of Search .................. 514/8, 12, 886, 514/887; 530/395; 424/89, 94.64; 435/23, 69.2, 236

[56] References Cited

U.S. PATENT DOCUMENTS

| | | | |
|---|---|---|---|
| 4,829,052 | 5/1989 | Glover et al. | 514/12 |
| 4,891,356 | 1/1990 | Szabo | 514/2 |
| 4,916,117 | 4/1990 | Lezdey et al. | 514/8 |
| 5,134,119 | 6/1992 | Lezdey et al. | 514/8 |
| 5,151,509 | 9/1992 | Kotowal et al. | 435/69.2 |
| 5,290,762 | 3/1994 | Lezdey et al. | 514/8 |

OTHER PUBLICATIONS

Ebina et al, *Microbiol. Immunol.*, vol. 35, No. 7, pp. 583–588, 1991.

Korant et al, *Biol. Chem. & Hopper–Syler*, vol. 369, Supp. pp. 281–286, May 1988.

Weber et al, *Science*, vol. 243, pp. 928–931, 17 Feb. 1989.

McNeeley et al, "Secretory Leukocyte Protease Inhibitor: A Human Saliva Protein Exhibiting Anti–Human Immunodeficiency Virus 1 Activity In Vitro" The Journal of Clinical Investigation, vo. '96, Jul. 1995, 456–464.

*Primary Examiner*—Howard E. Schain
*Assistant Examiner*—Abdel A. Mohamed
*Attorney, Agent, or Firm*—John Lezdey

[57] ABSTRACT

The present invention provides a method for inhibiting viral proliferation by preventing or inhibiting viral replication or killing the viruses on contact. Viral replication is prevented or inhibited through the use of serine protease inhibitors, their analogs, salts, conjugates or derivatives.

5 Claims, No Drawings

ANTIVIRAL COMPOSITIONS AND METHOD OF USE

This is a continuation-in-part of application Ser. No. 07/953,234, filed Sep. 30, 1992 of Lezdey et al., now abandoned, which is a continuation application of Ser. No. 08/122,204, filed Sep. 15, 1993, now U.S. Pat. No. 5,376,633.

FIELD OF THE INVENTION

The present invention relates to the inhibition of viral proliferation with human-type serum serine protease inhibitors. More specifically, the invention provides the prevention or inhibition of viral replication and in some instances a direct kill of the viruses through the use of human-type serine protease inhibitors, their analogs, salts, conjugates or derivatives. The viral replication is inhibited in mammals and plants and involves viruses with a DNA genome or a RNA genome.

BACKGROUND OF THE INVENTION

Infectious agents, such as viruses, bacteria, fungi, or protozoa, encode or carry their own crucial enzymes and nucleic acids which are obvious targets for intervention.

The viruses can be generally classified as being single stranded or double stranded. All viruses with a DNA genome except Pavoviridae are double stranded. Those viruses having RNA genomes are single or double stranded.

As a matter of convention, the nucleotide sequences found in viral messenger RNAs during replication are designated as having positive polarities. This allows RNA viruses to be classified as: 1) negative-stranded (–polarity) viruses, if they have genomes with nucleotide sequences complementary to those present in mRNAs; 2) positive-stranded (+ polarity) viruses, if they have genomes with identical sequences to mRNA; and 3) double-stranded RNA viruses, if they have RNA strands of both polarities. In addition to the polarity differences between viral RNA genomes, these viruses can be distinguished based on the segmentation of viral RNA.

The polarity of the RNA genome helps determine the mechanism of viral replication. Genomes of RNA viruses having single stranded RNAs of plus polarity are directly translated during the initial stages of infection by cell macromolecules without requiring the synthesis of specific viral transcriptases and other viral enzymes necessary for mRNA formation. Negative- and double-stranded viruses, however, require that transcription of mRNA from genome RNA occurs before translation can be initiated. Since normal cells lack an enzyme that transcribes RNA templates into complementary RNA strands, these viruses must encode the appropriate enzyme(s) during their replication cycle. Furthermore, the enzyme must be incorporated into progeny virus in order to initiate transcription and replication during successive infections.

The life cycle of retroviruses requires a specific protease that processes the precursor "gag" and "pol" polyproteins into mature virion components. If the protease is absent or inactive, non-infectious virus particles are produced.

All replicative competent viruses contain a minimum of three nucleotide sequence stretches that can be transcribed into protein without encountering a stop codon. These open reading frames are 1) "gag", which encodes virion core structural proteins; 2) "pol", which encodes the enzymes that catalyze the synthesis of viral DNA and its integration into host DNA; and 3) "env", which encodes the glycoproteins contained in the external and transmembrane virion envelope.

The retroviral life cycle begins when viral envelope proteins attach to specific receptors on the surface of susceptible cells. Reverse transcription of the single-stranded viral RNA genome(s) in the cytoplasm of infected cells leads to the formation of DNA-RNA heteroduplex consisting of the RNA plus strand and a DNA minus strand. The single stranded DNA then serves as a template, allowing the polymerase activity of reverse transcriptase to make a second DNA copy (the plus strand), whose sequence corresponds to that of the RNA contained in the core of the virus. The minus DNA strand is synthesized in a continuous fashion from a RNA primer, whereas the plus strand is synthesized discontinuously using multiple initiation sites. The viral genetic information now in the form of a double stranded, linear molecule or single strand linear molecule migrates to a cell nucleus where it is integrated into the host-cell genome. Following integration the viral DNA will be copied along with the cell's own genes every time the cell divides.

As the new virus comes from the host cells, one of the enzymes contained within the precursor polyprotein(s) cleaves itself from the precursor. This precursor is cleaved to produce the mature proteins, by the viral protease, which is itself a part of the precursor and becomes activated when the new progeny particles leave the surface of the infected cell.

Viruses which comprise negative-single stranded RNA genomes include Orthxomyoviridae, Rhabdoviridae, Paramyxoviridae, Bunyaviridae, and Arenaviridae.

Orthomyxoviridae, Bunyaviridae and Arenaviridae have segmented while Rhabdoviridae and Paramyxoviridae have unsegmented genomes.

Bunyaviridae include members of the Phlebovirus and Rotavirus which infects mammals, and the plant reoviruses, Phytoreovirus and Fijivirus.

Orthomyxoviridae includes the influenza viruses A, B and C.

Rhabdoviridae viruses are found in vertebrates as well as in plants. The genera Lyssavirus includes rabies virus and Vesiculovirus (vesicula stomatitis virus and chandipura virus).

Paramyxoviridae includes parainfluenza virus of mammals (mumps virus, Newcastle disease virus, etc.), Morbillivirus (the viruses of measles, canine distemper, etc.) and Pneumovirus (respiratory syctytial viruses of man and cattle).

Viruses which comprise positive single stranded RNA genomes include Picornaviridae, and Togaviridae.

Picornaviridae genera includes Enterovirus (Polioviruses, (Coxsackievirsus, Enterovirus 72 (hepatitis A), Cardiovirus (Encephalomyocarditis) Rhinovirus and Aphthovirus (foot and mouth disease of cattle).

Togaviridae genus includes Alphavirus (Sindbis virus, Semliki Forest virus), Flavivirus (Yellow fever virus, dengue virus, tick borne virus), Rubivirus (Rubella virus) and Pestivirus (Micosal disease virus).

Parvovirus is the only virus having a single stranded negative DNA genome. This virus primarily infects cats and dogs.

All the virus with a DNA genome with the exception of Pavoviridae are double stranded. These viruses include Papovaviradae, Adenoviridae, Herpesviridae, Iridoviridae, Poxviridae and Hepadnovidae.

Papovaviradae includes the genera Papillomavirus which infects humans with papilloma or wart virus and SV-40 like virus.

Adenoviridae comprises the two genus Mastadenovirus and Aviadenovirus of which Mastadenovirus infects mammals.

Herpesviridae and Alphaherpesvirinae include simplexvirus (herpes simplex types 1 and 2 which infects humans and Bovine mammillitis virus), Poikilovirus (pseudorabies virus) and Varicellavirus (human herpesvirus 3).

Hepadnaviridae includes the genus hepadnavirus (human hepatitis B virus, and mammalian hepatitis virus).

Poxviridae includes the genus orthopoxvirus which infects humans and animal poxvirus such as parapoxvirus and capripoxvirus.

U.S. Pat. No. 4,496,689, which is herein incorporated by reference, discloses conjugates of heparin, PVA or PEG (polyethylene glycol) which have active sites and can be used in the present invention.

U.S. Pat. No. 5,134,119 to Lezdey et al which is herein incorporated by reference, discloses the analogs of alpha 1-antitrypsin which can be used in the present invention.

U.S. Pat. No. 5,217,951 to Lezdey et al, which is herein incorporated by reference discloses the analogs, salts and derivatives of serine protease inhibitors for use in the treatment of non-bronchial mast cell implicated diseases.

U.S. Pat. No. 4,496,689 to Mitra, which is herein incorporated by reference discloses the preparation of complexes or conjugates of alpha 1-antitrypsin which can be used in the present invention.

Mammalian proteinase inhibitors are classified into families called kunins, kazals, ALPs (antileukoproteases), serpins, α-macroglobulins, cystatins and TIMPs (Tissue Inhibitors of Metalloproteinase).

Kunins include aprotinin, trypstatin and inter -α- trypsin inhibitor.

Serpins include alpha 1-antitrypsin inhibitor, alpha 1-antichymotrypsin, antithrombin, C 1-inhibitor, alpha 2- antiplasmin and Protein C-inhibitor.

Alpha 2-macroglobulin, although not a serpin, acts similarly to both alpa 1-antitrypsin and alpha 1-antichymotrypsin. This compound is considered as a scavenger which binds with those nucleotide groups, including aspartic groups, that are not picked up by the serpins.

Alpha 1-antichymotrypsin is considered by many as being misnamed since this inhibitor does not primarily bind with chymotrypsin but rather cathepsin G. Alpha 1-antitrypsin is the inhibitor with a preference for chymotrypsin as a binding partner.

It is to be understood that the term "conjugate" as used herein also refers to the complexes which may be formed, for example, with a polysaccharide polyol or protease (cathepsin G, elastase, etc) wherein the active sites of the protease inhibitor are retained.

SUMMARY OF THE INVENTION

The present invention relates to a method of treating viral infections and inflammations associated therewith in mammals and viral infections plants by the administration of serine protease inhibitors, their analogs, salts, conjugates or derivatives alone or in combination with other protease inhibitors which can bind to viral proteases that cause viral replication.

The activity of the serine proteases inhibitor in inhibiting or preventing viral replication is enhanced when used in connection with glutathione or other anti-viral antioxidants.

It is a general object of the invention to prevent or inhibit viral replication through the use of serine protease inhibitors.

It is also an object of the invention to kill viruses on contact utilizing serine protease inhibitors, especially serpins.

It is a further object of the invention to inhibit proteolytic cleavage of gag-pol precursor proteins of viruses utilizing serine protease inhibitors.

It is yet another object of the invention to provide a reduction of available enzyme sites for viral infiltration.

It is still another object of the invention to prevent or inhibit viral proliferation in mammals and plants.

DESCRIPTION OF THE PREFERRED EMBODIMENT

The present invention relates to the prevention or inhibition of viral proliferation through the use of serine protease inhibitors. The inhibitors provide multiple actions; namely, killing the virus on contact, inactivating the virus by binding to the core protein of the virus and/or binding to enzymes which may be available as host sites for viral infiltration.

The inhibitors of the invention are selected for use according to the particular virus having a nucleotide (peptide) sequence present which is capable of binding with an active sequence of the inhibitor, the nucleotide sequence of the viral protease or the nucleotide sequence of a host cell which may be involved in the transcription. The nucleotide sequence can be found in standard virology textbooks, for example, *Textbook of Human Virology* edited by Robert B. Belshe.

The inhibitor may bind with an amino acid sequence on the virus or the target protease of the virus, or both. A cocktail of the inhibitors can readily perform the desired binding when the virus is not known. That is, a combination of alpha-1 antitrypsin, alpha 1-antichymotrypsin and alpha 2-macroglobulin will bind with any one of a virus or viral target having a chymotryptic, tryptic or aspartic sequence.

During replication in some viruses, one of these sequences is exposed so that the virus can be bound and fail to undergo replication.

Serine protease inhibitors interfere with the replication cycle of the viruses so that other naturally occurring or added anti-viral compounds can act to kill or inactivate the viruses. It has been found that the combination of a serine protease inhibitor with glutathione can substantially reduce and/or inactivate viral infections when infused in mammals.

The serine protease inhibitors are effective for use in a suitable composition for treating plants and mammals for viral infections. It is understood that the serine protease inhibitors which are useful are naturally occurring, recombinant, glycosylated or non-glycosylated or mutagenized, (site-specific mutagenesis).

In mammals, serine protease inhibitors of the invention will maintain their viral killing activity even after binding with their natural proteases since the active anti-viral sites on the inhibitor molecule are still free to bind with or kill the virus. For example, alpha 1-antitrypsin when bound with cathepsin G still maintains antiviral activity.

Viruses having single stranded RNAs of plus polarity can be inactivated or killed on contact or during transcription by binding of the exposed nucleotide sequence with an active binding site of a protease inhibitor. Since many of the RNA viruses have a exposed chymotryptic sequence during transcription the protease inhibitor would preferably be a serpin such as alpha 1-antitrypsin. When the virus is not known, a mixture or "cocktail" of protease inhibitors would be preferred. A cocktail of protease inhibitors is also preferred when the viruses have already mutated. The mixture of inhibitors makes it difficult for the viruses to provide a defense against the mixture upon mutation. Alpha 2-macroglobulin having a plurality of active sites which bind with aspartic, chymotryptic and cysteine sequence is advantageously utilized when identification of the virus is not made. Furthermore, when the virus mutates, the inhibitor mixture is still effective since the mutation by the virus would only be against one of the inhibitors.

The human-type plasma serine protease inhibitors included in the present invention are alpha 1-antichymotrypsin, alpha 1-antitrypsin (alpha 1-proteinase inhibitor), alpha 2-macroglobulin, C-reactive protein, cystatin, tissue inhibitors of metalloproteinases (TIMP 1,2), alpha cysteine protease inhibitors, secretory leucocyte protease inhibitor and the like. The inhibitors of the invention may be natural or prepared by recombinant means. The inhibitors which are serpins are the most preferred.

Alpha 1-antitrypsin have been found to be effective in the prevention of the proliferation of viruses which either contain a chymotrypsin-like amino acid sequence in the nucleocapsid cores or uses a chymotrypsin-like enzyme as a host environment. The core protein is released as the first cleavage product of the viral replication cycle. The core particle is susceptible to inactivation by binding with the inhibitors. Viral proliferation is enhanced in the presence of proteases. The binding of proteases having chymotrypsin-like sequences with an inhibitor prevents viral proliferation through the proteases. Most viruses that have single-stranded RNA genomes code for proteinases that are members of the chymotrypsin family. Typical of the chymotryptic viruses are togaviruses which include alphaviruses. Alpha 1-antichymotrypsin is preferred for use in viral infections in mammals where T-cell activity is to be maintained.

Alpha 1-antichymotrypsin is preferable for use with viruses having a tryptic sequence in the virus core or target cell.

It is theorized that the absence of T-cells in infections such as AIDS is a result of the inactivation of T-cell receptors which fail to signal T-cell activation. The serine protease inhibitors of the invention, especially alpha 1-antitrypsin inhibitor can be used to prevent deactivation of the T-cell receptors by viral proteases.

Alpha 1-antitrypsin is also effective for use in connection with cysteine-active center proteases and trypsin-active-center proteases that are essential for virus maturation. Alpha 1-antitrypsin additionally blocks biosynthesis of tumor necrosis factor -α (TNF -α), a cytokine known to be involved in activation of HIV -1 in latently infected immune cells.

Cysteine-active center viral proteases have been identified in the sequenced genomes of four genera of the picornavirus family, the rhinoviruses (human rhinovirus strains 2–14 HRV2-14), the enteroviruses (human poliovirus (HPV1)), echovirus strain 9 (EV9), coxsackievirus (CXV), bovine enterovirus (BEV), and hepatitis A virus (HAV), cardioviruses (encephalomyelitis virus, and Theiler's murine encephalomyelitis virus (TMEV), and aphthoviruses (foot-and-mouth disease virus (FMDV)). Two different classes of plant viruses also encode cysteine proteases that are homologous to the picornaviral proteases, a comovirus with a bipartite genome, cowpea mosaic virus (CPMV), and two potyviruses with monopartite genomes, tobacco-etch virus (TEV) and tobacco-vein-mottling virus (TVMV). These proteases however also behave as serine proteases or are related through evolution.

In the treatment of viral infections of plants, the serine proteases can be applied by an aqueous spray or by inserting into the plant a serine protease inhibitor gene which can recombinantly produce the inhibitor so as to be present to prevent viral infiltration. For example, alpha 1-antitrypsin or alpha 2-macroglobulin gene can be inserted into tobacco plant to prevent the occurrence of tobacco mozaic virus. The inhibitors with sulfur groups are particularly useful for plant viruses.

The animal and plant viruses discussed above have in common a positive-strand RNA genome that is translated into a single large polyprotein (two in the case of the segmented CPMV. The precursor is proteolytically processed at preferred Gln-Gly and Tyr-Gly sites to release a number of mature proteins needed for virus replication, structure, and assembly. Binding with an inhibitor at or near these sites would therefore inhibit replication because the bulky groups would prevent entry into a host cell.

The specific viruses that can be treated with serine protease inhibitors having anti-chymotryptic characteristics such as alphavirus, flavivirus, rubivirus, sindbis virus, semliki forest virus, influenza A, B and C viruses, parvovirus, papillovirus, mastadenovirus, simplexvirus, cytomegalovirus, hepadnavirus, cardiovirus, phytorevirus, pneumovirus, HIV (AIDS), vesiculovirus, coronavirus and the like.

The viruses with a DNA genome in which the serpins of the invention are most effective include rhabdovirus, porvoviridae, papoviridae, orthomyxoviridae, herpesviridae, iridoviridae, poxviridae and hepadnaviridae.

Alpha 2-macroglobulin is one of the preferred protease inhibitors of the invention since it does not discriminate among the proteinase classes and it binds with chymotryptic sequences. Alpha 2-macroglobulin will bind or inhibit aspartic, trypsin and chymotrypsin-like enzymes. In addition, alpha 2-macroglobulin because of its binding with complements C3a and C5a, which are activated as a result of viral infections, reduces some of the symptoms of inflammation resulting from the viral infiltration in humans.

Infusible compositions of a compound of the invention are particularly suitable as high blood levels of the compound can occur after administration by infusion. Although intermuscular (IM) is also possible, high blood levels take longer to attain with IM.

The injectable solution of the compound of this invention for use in mammals may be made up in a sterile pyrogen-free liquid such as water, buffered saline or the like. There can be administered a weekly dose of about 60 mg/kg body weight and single doses of about 0.06 to 0.1 ml/kg body weight. A preferred daily dose is about 0.06 to 1.2 ml/kg body weight.

An alternative approach to administering the compounds of this invention is to utilize an injectable suspension. Such suspension may be made up in sterile water, sterile Saline or the like and may also contain suspending agents such as polyvinylpyrolidone, lecithin or the like (for example, in the manner described in Belgian Patent No. 839109). Alternatively, such compositions may be prepared in an acceptable oily suspending agent such as arachis oil or its equivalent or a liposome. Oral compositions using a liposome carrier can also be effective.

Compositions for topical application to skin and mucous membranes of mammals can be prepared as aqueous solutions, ointments, creams and the like utilizing conventional formulation techniques. However, aqueous compositions provide for enhanced penetration of the drug in topical use.

In the treatment of pulmonary viral infections such as influenza, administration of microcrystalline protease inhibitor by inhalation such as described in U.S. Pat. No. 4,916,117 is preferred.

The inhibitors of the invention particularly alpha 1-antitrypsin, in the purification of non-cellular blood components, especially plasma. The problem of the blood component products being infected with HIV or hepatitis virus can be overcome by antitrypsin, are useful in the deactivation of viruses in non-cellular blood components, about 50 to 300 mg of alpha 1-antitrypsin or to run the plasma through a column containing a conjugate or complex of alpha 1-antitrypsin so as to inactivate or kill the virus present or to ensure use of the plasma without infection of the patient.

The following examples further illustrate the practice of this invention, but are not intended to be limiting thereof. It will be appreciated that the selection of actual amounts of specific serine protease inhibitors to be administered to any individual patient (human or animal) will fall within the discretion of the attending physician and will be prescribed in a manner commensurate with the appropriate dosages which will depend on the stage of the disease and like factors uniquely within the purview of the attending physician.

EXAMPLE I

A topical cream for virally induced rashes or lesions in mammals was prepared as follows:

| A. The following mixture was prepared: | |
|---|---|
| α-1-antitrypsin | 9.0 mg |
| Olive oil | 1.0 mg |
| Cetanol | 2.0 mg |
| Stearic acid | 1.0 mg |
| Glycerin aliphatic acid ester | 12.0 mg |
| Tween 60 | 0.5 mg |
| B. The following mixture was also prepared: | |
| Propylene glycol | 0.5 mg |
| Methyl paraben | 0.1 mg |
| Propyl paraben | 0.02 mg |
| Purified water | to 100 mg in total |

The mixture of parts A and B were blended together by conventional means to give a total of 100 mg. of 100% by weight topical cream which could be utilized for treatment of herpes simplex and other inflammatory dermatological conditions associated with the disease. If desired, secretory leucocyte protease inhibitor and/or alpha 2-macroglobulin as well as a corticosteroid may be added in an amount of 1.0 mg to part A.

EXAMPLE II

An olegenous anhydrous ointment for topical administration was prepared with the following composition:

| Composition | % |
|---|---|
| α-1-antitrypsin | 5.0 |
| Soy phosphatide | 4.0 |
| Plastibase 50W | 89.00 |
| Glutathione | 2.0 |
| | 100.00 |

If desired, in lieu of alpha 1-antitrypsin as the active principal, there may utilized the combination of alpha 1-antichymotrypsin and alpha 1-antitrypsin. Other non-aqueous lipid miscible carriers may also be utilized. The composition may be used in combination with a topical corticosteroid. The composition can be used for treating herpes zoster.

EXAMPLE III

A suitable 5% cream for topical use was prepared by admixing 1 g of PROLASTIN from Cutter Biological Laboratories, with 6 ml of water and 20 g of a balm available under the trademark AQUAPHOR, sold by Beiesdorf Inc., Norwalk, Conn. AQUAPHOR comprises a mixture of petrolatum, mineral oil, and wool alcohol.

The cream is useful for minor irritations and in the treatment of viral infections which produced skin lesions or rashes.

EXAMPLE IV

A pilot study was performed with five patients suffering from herpes simplex I wherein the skin rash resulting from the virus was treated daily with a 15% solution of alpha 1-antitrypsin followed by a 10% cream formed using alpha 1-antitrypsin and AQUAPHOR. After two days, in all five patients the inflammation and the rash were significantly reduced and after four days the rash had disappeared. The 15% solution had enhanced activity.

EXAMPLE V

Human rhinovirus strain 2 was propagated on Eagle's minimum essential medium supplemented with 5% fetal calf serum. The virus cells were suspended in two 1 ml aliquots containing $10^{-4}$M α 1-chymotrypsin. To one of the aliquots was added $10^{-4}$M α 1-antichymotrypsin. The cultures were incubated at 37° C. The cultures were fixed with methanol and stained with GIEMSA 7 to 20 h later. The fusions were counted through a microscope.

A 1.5 to threefold increase in fusion occurred with α-chymotrypsin treated medium over the non-treated medium. In the medium treated with both α-chymotrypsin and α1-antichymotrypsin only low titers of virus were noted ($10^{1.5}$TCID$_{50}$/ml).

EXAMPLE VI

Vesicular stomatitis virus (VSV) which is considered as representative of the replication schemes of unsegmented, negative stranded RNA and as a model for studying defective-interfering (DI) particles was used in the following test.

Vesicular stomatitis virus, Sindbis virus and Pararabies virus are considered as being representative models for hepatitis viruses and a kill of each virus would be considered indicative as a kill on contact of hepatitis viruses.

A. Viral Inactivation Protocol for VSV, Sindbis, and Pseudorabies Virus 1 plaque=1 virus. The VSV stock in $10^7$ PFU/ml was Indianna strain. Target cells were VERO African Green Monkey Kidney cells.

1. Alpha 1-antitrypsin was reconstitute in 10 ml of sterile $H_2O$. To 8.1 ml of the was added 0.9 ml VSV, which should result in about $10^8$ titer PFU/ml. To 0.4 ml of the mixture was added albumin, and iodine (in that order) to reach a final volume of 2 ml. The mixture was incubate for 30 minutes. After incubation, ascorbate was added to quench the reaction.

2. Plates containing green monkey kidney cells which have grown about 2 days, were utilized. To prepare the plates, dilute 0.5 ml of the incubated sample 1:10 in RPMI-1640 medium followed by dilutions to get into the desired range for reading ($10^{-5}$, $10^{-6}$, etc) was used, 250 ul was added to each well in duplicate to the plate and put at 37° C. in 5% $CO_2$. The mixture was rocked or shaken every 15 minutes.

3. The virus settled onto the monolayer and initiated the infection of the VERO cells. After 45 minutes, the remaining liquid (spent medium, spent virus) was removed. All of the active virus should remain attached. The plates consisted of 2% agarose +2× medium without pH indicator (clear). The 2% agarose prevents the virus from spreading over the entire plate and infecting all of the cells. 2–3 ml of agarose was used. The virus travels cell to cell via membranes.

4. Three days later the cells were laid over with 1% agarose with neutral red dye and incubated overnight while the dye diffuses into the cells (the live VERO cells only). Therefore, a red monolayer with white plaques was noted.

B. Inactivation of VSV by alpha 1-antitrypsin inhibitor (ATT)

Following the procedure of Part A:

| | ATT | .02 M Tris mg/ml | VSV mg/ml | Incubator Time (min.) |
|---|---|---|---|---|
| 1. Control | 0 | .09 | 0.1 | 60 |
| 2. ATT | 3 mg | .09 | 0.1 | 60 |
| 3. ATT | 0.05 mg | .09 | 0.1 | 60 |
| 4. ATT | 3 mg | .09 | 0.1 | 30 |
| 5. ATT | 0.05 mg | .09 | 0.1 | 30 |
| 6. Control | 0 | .09 | 0.1 | 30 |

| | | Results | | |
|---|---|---|---|---|
| 1. | $10^{-4}$ | T | T | $3.6 \times 10^7$ |
| | $10^{-5}$ | 88 | 90 | |
| | $10^{-6}$ | 6 | 3 | |
| 2. | $F_s$ | 0 | 0 | <2 |
| | $10^{-1}$ | 0 | 0 | |
| | $10^{-2}$ | 0 | 0 | |
| 3. | $F_s$ | T | T | Too numerous to count |
| | $10^{-1}$ | T | T | |
| | $10^{-2}$ | T | T | |
| 4. | $F_s$ | 0 | 0 | <2 |
| | $10^{-1}$ | 0 | 0 | |
| | $10^{-2}$ | 0 | 0 | |
| 5. | $F_s$ | T | T | Too numerous to count |
| | $10^{-1}$ | T | T | |
| | $10^{-2}$ | T | T | |
| 6. | $10^{-4}$ | T | T | $1.2 \times 10^7$ |
| | $10^{-5}$ | T | T | |
| | $10^{-6}$ | T | T | |

EXAMPLE VII

Inactivation of Sindbis virus (SBV) and Pseudorabies virus (PRV).

Following the procedure of Example VI alpha 1-antitrypsin (ATT) was used to determine antiviral activity against Sindbis virus (SBV) mg/ml and Pseudorabies virus (PRV) mg/ml.

To 8.258 mg/vial of ATT was added 1.65 ml of water to obtain a 5mg/ml solution. Incubation time in each case was 30 minutes.

| | ATT ml | 0.02M Tris ml | SBV | PRV |
|---|---|---|---|---|
| 1. Control | — | 1.0 | 0.1 | |
| 2. 1 mg-ATT | 0.22 | 0.88 | 0.1 | |
| 3. 2 mg-ATT | 0.44 | 0.66 | 0.1 | |
| 4. 0.5 mg-ATT | 0.66 | 0.44 | 0.1 | |
| 5. Control | | 1.0 | | 0.1 |
| 6. 1 mg-ATT | 0.22 | 0.88 | | 0.1 |
| 7. 1.5 mg-ATT | 0.33 | 0.77 | | 0.1 |

| | | Results | | |
|---|---|---|---|---|
| 1. | $10^{-4}$ | T | T | $6.7 \times 10^7$ |
| | $10^{-5}$ | 1 to 5 | 170 | |
| 2. | $F_s$ | 0 | 0 | |
| | $10^{-1}$ | 0 | 0 | |
| | $10^{-2}$ | 0 | 0 | |
| 3. | $F_s$ | 0 | 0 | |
| | $10^{-1}$ | 0 | 0 | |
| | $10^{-2}$ | 0 | 0 | |
| 4. | $F_s$ | 0 | 0 | |
| | $10^{-1}$ | 0 | 0 | |
| | $10^{-2}$ | 0 | 0 | |
| 5. | $6 \times 10^4$ | PFU/ml | | |
| 6 | $F_s$ | T | T | |
| | $10^{-1}$ | some plaque | some plaque | some plaque |
| | $10^{-2}$ | 0 | 0 | |
| 7. | $F_s$ | T | T | $1.8 \times 10^3$ |
| | $10^{-1}$ | 49 | 40 | |
| | $10^{-2}$ | 3 | 2 | |

$F_s$ = full strength
T = too numerous to count

EXAMPLE VIII

Following the procedure of Examples VI and VII alpha 1-antichymotrypsin (ACT) and inter-alpha-trypsin inhibitor (ITI) were tested against VSV, Sindbis and Pseudorabies Virus.

| VSV | Sindbis | Pseudorabies |
|---|---|---|
| 1. Control | 4. Control | 7. Control |
| 2. 9 Mg ACT | 5. 9 Mg ACT | 8. 9 Mg ACT |
| 3. 9 Mg ITI | 6. 9 Mg ITI | 9. 9 Mg ITI |

| | | Results | | |
|---|---|---|---|---|
| 1. | $10^{-4}$ | T | T | $1.6 \times 10^{-7}$ |
| | $10^{-5}$ | 42 | 36 | |
| | $10^{-6}$ | 4 | 3 | |
| 2. | $F_s$ | T | T | |
| | $10^{-1}$ | T | T | |
| | $10^{-2}$ | T | T | |
| 3. | $F_s$ | T | T | |
| | $10^{-1}$ | T | T | |
| | $10^{-2}$ | T | T | |
| 4. | $10^{-4}$ | 29 | 43 | $7.2 \times 10^5$ |
| | $10^{-5}$ | 5 | 5 | |
| | $10^{-6}$ | 0 | 0 | |
| 5. | $F_s$ | T | T | |
| | $10^{-1}$ | T | T | |
| | $10^{-2}$ | T | T | |
| 6. | $F_s$ | T | T | |
| | $10^{-1}$ | T | T | |
| | $10^{-2}$ | T | T | |

| | | | | |
|---|---|---|---|---|
| 7. | $10^{-1}$ | T | T | $3.7 \times 10^4$ |
| | $10^{-2}$ | 88 | 100 | |
| | $10^{-3}$ | 10 | 7 | |
| 8. | $F_s$ | T | T | |
| | $10^{-1}$ | T | T | |
| | $10^{-2}$ | T | T | |
| 9. | $F_s$ | T | T | |
| | $10^{-1}$ | T | T | |
| | $10^{-2}$ | T | T | |

CONCLUSION

Neither alpha 1-antichymotrypsin or inter-alpha-trypsin inhibitor were active against the viruses.

EXAMPLE IX

Following the procedure of Example VI Shope fibroma virus (SFV) was treated with alpha 1-antichymotrypsin (ACT).

SFV (0.1 mg/ml)

1. Control
2. ACT 3 mg (30 min)
3. ACT 3 mg (60 min)

Results

| | | | | |
|---|---|---|---|---|
| 1. | $10^{-1}$ | T | T | $3.7 \times 10^4$ |
| | $10^{-2}$ | 88 | 100 | |
| | $10^{-3}$ | 10 | 7 | |
| 2. | $F_s$ | 0 | 0 | |
| | $10^{-1}$ | 0 | 0 | |
| | $10^{-2}$ | 0 | 0 | |
| 3. | $F_s$ | 0 | 0 | |
| | $10^{-1}$ | 0 | 0 | |
| | $10^{-2}$ | 0 | 0 | |

Serpins are the most important of the inhibitors with α 1-antitrypsin preferred for general virus. α1-antichymotrypsin being useful for tumor virus.

What is claimed is:

1. A method for the inhibition of viral proliferation which comprises treating a patient with a composition containing an antiviral effective amount of a human-type serine protease inhibitor selected from the group consisting of alpha 1-antitrypsin, secretory leucocyte protease inhibitor and alpha 1-antichymotrypsin.

2. The method of claim 1 wherein said serine protease inhibitor is alpha 1-antitrypsin.

3. The method of claim 1 wherein said serine protease inhibitor is secretory leucocyte protease inhibitor.

4. The method of claim 1 wherein said serine protease inhibitor binds with a viral aspartic protease or its target cell.

5. The method of claim 1 wherein said serine protease inhibitor inhibits proteolytic cleavage of gag-pol precursor proteins.

* * * * *